United States Patent [19]

Fujishima et al.

[11] Patent Number: 5,702,939

[45] Date of Patent: Dec. 30, 1997

[54] GLUCOSAMINE-6-PHOSPHATE DEAMINASE AND PROCESS FOR PRODUCING THE SAME

[75] Inventors: Shizu Fujishima; Naoko Yamano, both of Ikeda, Japan

[73] Assignee: Agency of Industrial Science & Technology, Tokyo, Japan

[21] Appl. No.: 612,491

[22] Filed: Mar. 7, 1996

[30] Foreign Application Priority Data

Apr. 25, 1995 [JP] Japan ................................. 7-125787

[51] Int. Cl.⁶ .............................. C12N 9/90; C12N 9/78; C12N 9/80

[52] U.S. Cl. ......................... 435/233; 435/195; 435/227; 435/228; 435/252.1; 435/909

[58] Field of Search .............................. 435/233, 227, 435/228, 195, 909, 252.1

[56] References Cited

U.S. PATENT DOCUMENTS 5,252,468  10/1993  Fujishima et al. ................ 435/71.1

OTHER PUBLICATIONS

Gopal et al. Journal of General Microbiology. 128(10). 1992. pp. 2319–2326.

Comb et al. Journal of Biol. Chem. 232. 1958. pp. 807–827.

*Primary Examiner*—Leon B. Lankford, Jr.
*Attorney, Agent, or Firm*—Nikaido, Marmelstein, Murray & Oram LLP

[57] ABSTRACT

A glucosamine 6-phosphate deaminase having specific physicochemical properties. A process for producing the glucosamine 6-phosphate deaminase which comprises incubating a microorganism belonging to the genus Vibrio and harvesting the glucosamine 6-phosphate deaminase from the culture thus obtained.

3 Claims, 1 Drawing Sheet

GLUCOSAMINE-6-PHOSPHATE DEAMINASE AND PROCESS FOR PRODUCING THE SAME

BACKGROUND OF THE INVENTION

This invention relates to a glucosamine 6-phosphate deaminase which is an enzyme acting on the amino group of D-glucosamine 6-phosphate to thereby form D-fructose 6-phosphate and a process for advantageously producing the same.

Glucosamine-6-phosphate deaminase is an enzyme indispensable for the metabolic pathway of sugars. It has been employed as a diagnostic agent or in the field of genetic engineering, etc. It is therefore believed that glucosamine-6-phosphate deaminase can contribute to the medical and industrial fields. Moreover, D-fructose 6-phosphate formed by this enzyme is valuable as a reaction substrate or a reference material.

Little information has been accumulated so far on the production of this enzyme. Namely, there has been reported nothing but the production of this enzyme originating in Escherichia or *Candida albicans* on a laboratory scale. Thus there has not been established hitherto any technique which is applicable to the production of this enzyme on an industrial scale.

SUMMARY OF THE INVENTION

It is an object of the present invention to provide a glucosamine-6-phosphate deaminase having specific physicochemical properties.

It is another object of the present invention to provide an advantageous process whereby a large amount of the glucosamine-6-phosphate deaminase can be produced on an industrial scale.

The present inventors have conducted extensive studies in order to provide the above-mentioned process. As a result, they have successfully found out that a bacterium belonging to the genus Vibrio can inductively produce a large amount of a glucosamine-6-phosphate deaminase, thus completing the present invention. Accordingly, the process for producing glucosamine-6-phosphate deaminase according to the present invention comprises incubating a microorganism which belongs to the genus Vibrio and is capable of producing glucosamine-6-phosphate deaminase and harvesting the glucosamine-6-phosphate deaminase from the culture thus obtained.

DESCRIPTION OF THE PREFERRED EMBODIMENTS

Figure 1:
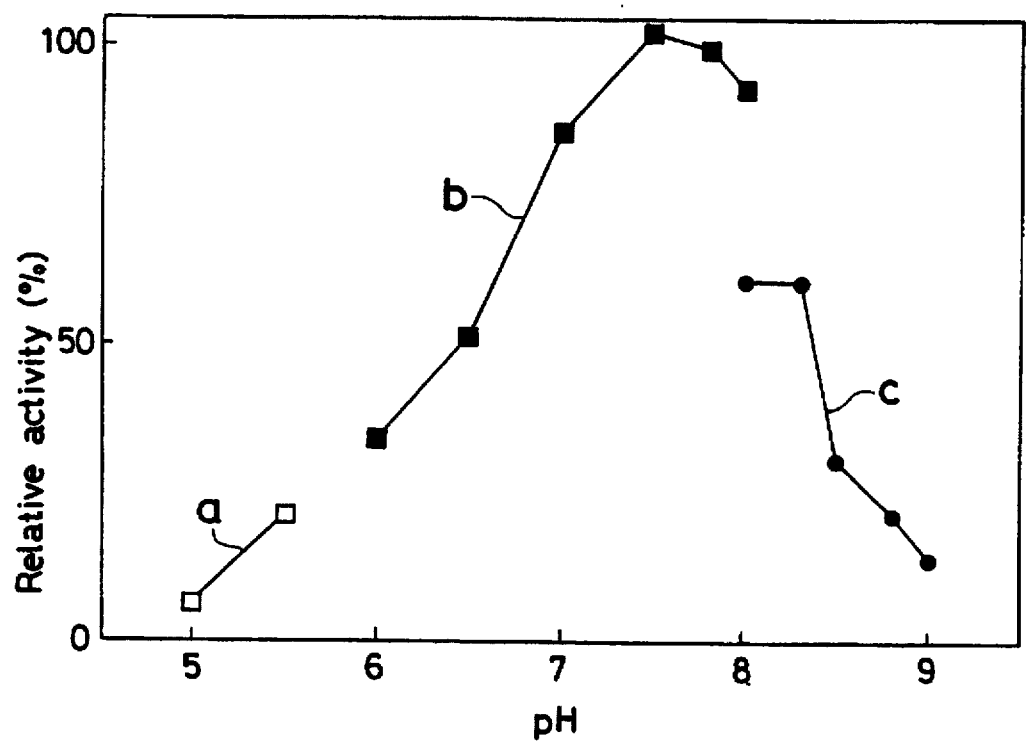
FIG. 1 is a graph which shows the relationship between the relative activity (%) of the glucosamine-6-phosphate deaminase originating in Vibrio in a buffer and the pH value, thus giving the optimum pH curve of this enzyme.

The glucosamine-6-phosphate deaminase-producing microorganism to be used in the present invention is a strain belonging to the genus Vibrio, for example, *Vibrio cholerae* non-O1. This strain *Vibrio cholerae* non-O1 has been deposited with INSTITUTE FOR FERMENTATION, OSAKA (IFO), 2-chome, Yodogawa-ku, Osaka 532, Japan under the accession number IFO 15429.

Now, a process for producing the glucosamine 6-phosphate deaminase and the characteristics of this enzyme will be described in detail by taking the case with the use of *Vibrio cholerae* non-O1 as a glucosamine 6-phosphate deaminase-producing strain.

Glucosamine-6-phosphate deaminase may be produced by inoculating the above-mentioned strain into an appropriate medium and incubating the same in the presence of an inducer in accordance with the conventional method. As the inducer, use can be made of chitin, decomposition products of chitin, N-acetyl-D-glucosamine, N-acetyl-D-glucosamine oligomers or a mixture thereof. The inducer is added to give a concentration of at least 0.1 g/l, preferably from 1.0 to 50 g/l. As the medium, any publicly known one is usable. For example, use can be made of glucose, maltose, xylose, sucrose, peptone, etc., as a carbon source, while use can be made of organic nitrogen substances such as yeast extract, peptone, meat extract and amino acid solutions or inorganic nitrogen substances such as ammonium sulfate and ammonium chloride as a nitrogen source. It is also possible to use the inducer as a carbon source or a nitrogen source. As inorganic salts, use can be made of magnesium sulfate, magnesium chloride, sodium phosphate, potassium phosphate, potassium chloride, sodium chloride, calcium chloride, etc., in an appropriately combined form.

The pH value of the above-mentioned medium is regulated within a range of from 6.5 to 8.0 by adding an appropriate acid or base thereto. Then the medium is sterilized under elevated pressure. The incubation temperature ranges from 25° to 40° C., preferably from 32° to 38° C. The strain is incubated at this temperature for 12 to 48 hours under aeration/agitation or shaking. It may be incubated in a plate medium which optionally contains the above-mentioned carbon source, nitrogen source and inorganic salts together with agar at a temperature of from 25° to 40° C., preferably from 32° to 38° C., for 15 to 120 hours. Alternatively, this strain may be cultured under static conditions.

The culture thus obtained may be divided into the culture medium and the cells by any conventional method such as centrifugation or filtration. It is appropriate to select centrifugation therefor. When a plate medium is used, the cells may be collected merely by using a spatula. The enzyme thus accumulated in the cells may be extracted by any method which has been employed in the art, for example, ultrasonic disruption of the cells, disruption of the cells with the use of a Dynomil in which the cells are rotated together with glass beads, or destruction of the cell membrane by using an enzyme such as lysozyme or an organic solvent such as toluene. The enzyme can be obtained by extracting from the cells by selecting an appropriate method from those cited above.

From the crude enzyme solution thus obtained, the glucosamine-6-phosphate deaminase may be further purified, if required, by appropriately combining procedures commonly employed for the purification of enzymes, for example, ammonium sulfate precipitation, ion exchange column chromatography, gel filtration, adsorption chromatography, hydrophobic chromatography, preparative electrophoresis, etc.

The glucosamine-6-phosphate deaminase obtained by the present invention is a novel one which originates in a bacterium belonging to the genus Vibrio and has the physicochemical properties (1) to (6) as described below.

(1) Function

It acts on the amino group of D-glucosamine 6-phosphate to thereby form D-fructose 6-phosphate.

(2) Substrate specificity

It acts on D-glucosamine 6-phosphate but not on D-glucosamine.

(3) Optimum pH value 7.4 to 7.8 (shown in FIG. 1). In FIG. 1, a stands for the case of a 50 mM acetic acid/sodium acetate buffer containing the glucosamine-6-phosphate deaminase; b stands for the case of a 50 mM potassium dihydrogenphosphate/sodium dihydrogenphosphate buffer containing the glucosamine-6-phosphate deaminase; and c stands for the case of a 40 mM boric acid/sodium hydroxide buffer containing the glucosamine-6-phosphate deaminase. As FIG. 1 shows, the highest relative activity (%) is achieved in the 50 mM potassium dihydrogenphosphate/sodium dihydrogenphosphate buffer and the highest relative activity (%) is obtained at pH 7.4 to 7.8. It is therefore recommended to use the 50 mM potassium dihydrogenphosphate/sodium dihydrogenphosphate buffer as a buffer.

(4) Stable pH value 7.0 to 9.0 (after incubating at 37° C. for 30 minutes, at least 70% of the activity is sustained).

(5) Optimum temperature

37° to 38° C. (shown in FIG. 2)

Figure 2:
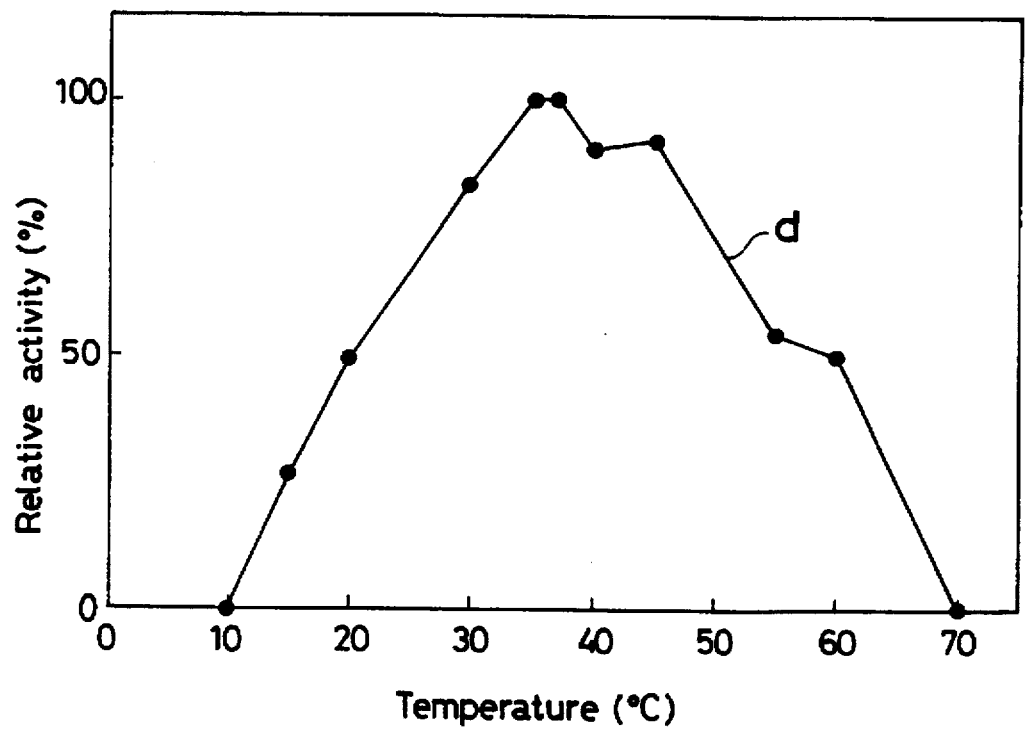
FIG. 2 is a graph which shows the relationship between the relative activity (%) of the glucosamine-6-phosphate deaminase originating in Vibrio in a buffer and the temperature (°C.), thus indicating the temperature dependency of this enzyme.

In FIG. 2, d stands for the case of a 40 mM boric acid/sodium hydroxide buffer containing the glucosamine-6-phosphate deaminase. As FIG. 2 shows, the highest relative activity (%) is achieved at 37° to 38° C.

(6) Heat stability

50° C. (after incubating at pH 7.5 for 30 minutes, at least 70% of the activity is sustained).

(7) Method for measuring activity

To 0.39 ml of a 1/15M phosphate buffer (pH 7.5) is added 0.1 ml of a 1.0% solution of D-glucosamine-6-phosphate as a substrate. Further, 0.01 ml of an enzyme solution is added thereto followed by the incubation at 37° C. for 10 minutes. Then the unreacted D-glucosamine-6-phosphate is colorimetrically determined by the indole/hydrochloric acid method. The amount of the enzyme by which 1 μmol of D-glucosamine-6-phosphate can be deaminated in 1 minute is referred to as 1 unit (U).

It has been reported that the glucosamine 6-phosphate deaminase obtained from *Candida albicans* is inactivated when treated at 50° C. for 5 minutes [Krishnamurthy Nattrajan and Asis Datta, The Journal of Biological Chemistry, 268, 9206–9214 (1993)]. Compared with this deaminase originating in Candida, the glucosamine-6-phosphate deaminase of the present invention has an apparently improved stability.

To further illustrate the present invention in greater detail, the following Example will be given.

EXAMPLE

A plate medium (pH 7.4) which contained, per 200 ml of the medium, 0.6 g of ammonium nitrate, 0.2 g of dipotassium hydrogenphosphate, 2 g of sodium chloride, 0.12 g of magnesium sulfate, 0.02 g of calcium chloride, 10 g of glucose and 3 g of agar was inoculated with a strain (IFO 15429) belonging to *Vibrio cholerae* non-O1. After incubating at 37° C. for 24 hours, the cells were collected with the use of a sterilized spatula and added to a liquid medium (pH 7.4) containing 25 g of N-acetyl-D-glucosamine in 500 ml of a commercially available Marine broth (mfd. by Difco). After mixing, the cells were incubated at 37° C. for 24 hours while shaking under aerobic conditions.

Then the culture medium was centrifuged at 10,000×g for 15 minutes to thereby give 10 g, on a wet basis, of cells. The cells thus obtained were suspended in 20 ml of physiological saline and sonicated at 0° C. for 10 minutes (operation time of 20 seconds and suspension time of 20 seconds). Then it was centrifuged to thereby give a cell-free extract having a specific activity of glucosamine-6-phosphate deaminase of 0.309 U/mg protein and the total activity thereof of 380 U.

Subsequently, the extract was injected into a DEAE Bio-Gel A column (mfd. by Bio-Rad) which had been equilibrated with a 10 mM phosphate buffer (pH 7.0) and the concentration of sodium chloride was elevated stepwise. Thus 10 ml of an eluate containing 47 mg of a protein having a specific activity of 5.38 U/mg protein was obtained with the use of 200 mM sodium chloride. This eluate was further injected into a hydroxylapatite column and the concentration of the phosphate buffer was elevated stepwise to thereby elute the target enzyme. Thus 4 ml of a solution containing 5.5 mg of a protein having a specific activity of 34.4 U/mg protein was obtained with the use of a 10 mM phosphate buffer. Thus this enzyme was purified 111-fold and the activity was recovered in a yield of 49%.

As described above, the present invention provides the technique by which a glucosamine-6-phosphate deaminase with an excellent stability can be produced in a large amount on an industrial scale. The glucosamine-6-phosphate deaminase according to the present invention plays an important role in the metabolic pathway of sugars. Also, it has been employed as a diagnostic agent or in the field of genetic engineering, etc. Accordingly, it is widely usable in the medical and industrial fields. Moreover, the D-fructose 6-phosphate formed by the glucosamine-6-phosphate deaminase of the present invention is valuable as a reaction substrate or a reference material.

What is claimed is:

1. An isolated and purified glucosamine-6-phosphate deaminase which is produced by a microorganism belonging to the genus Vibrio and identified on the basis of the following physicochemical properties:

(1) function:
      acting on the amino group of D-glucosamine 6-phosphate to thereby form D-fructose 6-phosphate;

(2) substrate specificity:
      acting on D-glucosamine 6-phosphate but not on D-glucosamine;

(3) optimum pH value:
      7.4 to 7.8;

(4) stable pH value:
      7.0 to 9.0 (after incubating at 37° C. for 30 minutes, at least 70% of the activity is sustained);

(5) optimum temperature:
      37° to 38° C; and (6) heat stability:
      50° C. (after incubating at pH 7.5 for 30 minutes, at least 70% of the activity is sustained).

2. A process for producing a glucosamine-6-phosphate deaminase which comprises incubating a microorganism belonging to the genus Vibrio and capable of producing a glucosamine-6-phosphate deaminase and harvesting the glucosamine-6-phosphate deaminase from the culture thus obtained.

3. A process for producing a glucosamine-6-phosphate deaminase as set forth in claim 2 wherein said microorganism is *Vibrio cholerae* non-O1.

* * * * *